United States Patent [19]

Thiel et al.

[11] Patent Number: 5,344,643
[45] Date of Patent: Sep. 6, 1994

[54] SHAMPOO-CONDITIONING COMPOSITION AND METHOD OF MAKING

[75] Inventors: Dawn M. Thiel, St. Louis Park; James M. Wilmott, Plymouth; John R. Kaysen, Fridley, all of Minn.

[73] Assignee: Dowbrands L.P., Indianapolis, Ind.

[21] Appl. No.: 112,638

[22] Filed: Aug. 27, 1993

Related U.S. Application Data

[63] Continuation of Ser. No. 847,852, Mar. 9, 1992, abandoned, which is a continuation of Ser. No. 633,581, Dec. 21, 1990, abandoned.

[51] Int. Cl.$^5$ ............................................. A61K 7/075
[52] U.S. Cl. ............................................. 424/70; 424/71; 424/74; 424/401; 424/78.31; 424/195.1; 514/938; 514/881; 252/DIG. 13
[58] Field of Search ............ 424/70, 71, 74, 401, 424/78.31, 195.1; 514/938, 881; 252/DIG. 13

[56] References Cited

U.S. PATENT DOCUMENTS

| | | | |
|---|---|---|---|
| 3,718,609 | 2/1973 | Weimer | 252/545 |
| 3,950,510 | 4/1976 | Adams | 424/70 |
| 4,364,837 | 12/1982 | Pader | 252/DIG. 13 |
| 4,491,539 | 1/1985 | Hoskins | 252/541 |
| 4,678,606 | 7/1987 | Akhter et al. | 252/542 |
| 4,686,254 | 8/1987 | Lockhead | 424/70 |
| 4,788,006 | 11/1988 | Bolich | 424/70 |
| 4,810,407 | 3/1989 | Sandvick | 252/90 |
| 4,925,659 | 5/1990 | Grollier | 424/70 |
| 4,933,176 | 6/1990 | Van Reeth | 424/70 |
| 5,085,857 | 2/1992 | Reid et al. | 424/70 |

FOREIGN PATENT DOCUMENTS

| | | |
|---|---|---|
| 2404607 | 2/1973 | France. |
| 50-10700 | 8/1975 | Japan. |
| 56-12930 | 3/1980 | Japan. |

*Primary Examiner*—Thurman K. Page
*Assistant Examiner*—Raj Bawa

[57] ABSTRACT

Disclosed is an anionic shampoo-conditioning composition comprising an oily conditioning agent, a shampooing agent, a carboxyvinyl polymer, a cationic conditioning agent, and water. The carboxyvinyl polymer has a large proportion of carboxyl monomeric groups and a small proportion of long-chain alkyl monomeric units, and is crosslinked to a small degree. Further disclosed is a process for making the above composition and a method for applying it to hair. The composition provides enhanced conditioning properties utilizing both oily and cationic conditioning agents in combination with an anionic carboxyvinyl polymer while maintaining stability and dispersion.

17 Claims, No Drawings

SHAMPOO-CONDITIONING COMPOSITION AND METHOD OF MAKING

CROSS-REFERENCE TO RELATED APPLICATIONS

This is a continuation of application Ser. No. 07/847,852 which was filed Mar. 9, 1992, now abandoned, which is a continuation of application Ser. No. 633,581 filed Dec. 21, 1990, now abandoned.

The present invention relates to a stable shampoo composition providing enhanced conditioning and stability properties and a method of preparation therefor.

BACKGROUND

Hair care compositions which claim to impart both shampoo and conditioner properties to the hair at the same time are well known in the art. Such compositions typically contain one or more surfactants for shampooing or cleaning purposes and one or more "conditioning" agents for the purpose of making hair easier to comb when wet, and more controllable, that is less static and more manageable, when dry. Typically, these conditioning agents are either water-insoluble oils or cationic resinous materials or surfactants.

Prior art shampoo-conditioning compositions however, exhibit stability and performance problems because the shampooing agents and the conditioning agents may interfere with the performance of each other. This interference has required that tradeoffs be made between shampooing and conditioning.

A problem with prior art shampoo-conditioning compositions is that cationic resinous materials and surfactants commonly employed as conditioning agents may inactivate or be inactivated by anionic surfactants commonly employed as shampooing agents; thus, the performance of either or both of the shampooing or conditioning agents may be negatively affected by the other. The prior art has attempted to solve this problem by incorporating the cationic materials or surfactants in shampoo systems utilizing nonionic, amphoteric, or cationic cosurfactants as shampooing agents, but these systems do not deliver as desirable a level of cleaning or foaming as do anionic shampoo systems. The prior art has also attempted to solve the problem of incompatibility of the shampooing and conditioning agents by limiting the concentration of cationic conditioning agents to levels in which such problems are minimized; this limitation impedes the conditioning efficacy of prior art compositions.

Another problem associated with prior art shampoo-conditioning compositions is that cationic resinous materials and surfactants commonly employed as conditioning agents may be inactivated by or be incompatible with anionic carboxyvinyl polymers commonly employed as thickening and suspending agents. The prior art has attempted to solve this problem by limiting the level of cationic conditioning agents to a level in which inactivation or incompatibility problems are minimized; this limitation impedes the conditioning efficacy of prior art compositions.

Another problem associated with prior art shampoo-conditioning compositions is that waterinsoluble oils such as vegetable oils commonly employed as conditioning agents are incompatible with surfactants, especially anionic surfactants, utilized as shampooing agents. This incompatibility may be manifest in a lack of homogeneity in the composition or in inadequate shelf life for the same.

U.S. Pat. Nos. 4,686,254, 4,788,006, 4,491,539, 3,964,500 and 3,969,500 are representative of prior art compositions which attempt to address the problems described above, but which fail in some aspect of conditioning performance, shampooing performance, or shelf-stability. None permit the combination of oily conditioning agents, cationic conditioning agents, anionic carboxyvinyl polymers, and shampooing agents particularly anionic surfactants, to form a composition having the desired characteristics described above.

Accordingly, it would be desirable to have a shampoo-conditioning composition providing both enhanced shampooing and conditioning without compromising shelfstability. Further, desirably, the composition utilizes both oily conditioning agents and cationic conditioning agents to provide enhanced conditioning. Further, desirably, the composition utilizes an oily conditioning agent which is natural, biodegradable, inexpensive, and readily available. Further, desirably, such oily conditioning agent will be suspendable and stabilizable with an anionic carboxyvinyl polymer commercially available at uniform activity levels. Further, desirably, the carboxyvinyl polymer will be compatible with and not inactivate the cationic conditioning agent or agents. Further desirably, such conditioning agents may be incorporated into an anionic shampoo system.

Heretofore, compositions utilizing cationic conditioning agents and anionic carboxyvinyl polymers as thickening and suspending agents have been difficult to prepare due to the incompatibility of the two substances as discussed above. Accordingly, it would be desirable to have a process for preparing such compositions wherein the incompatibility problem is circumvented.

SUMMARY OF THE INVENTION

According to the present invention, there is a shampoo-conditioning composition comprising an oily, substantially water-insoluble conditioning agent, a shampooing agent, an amount of a carboxyvinyl polymer sufficient to suspend and stabilize the oily conditioning agent, a cationic conditioning agent, and water. The carboxyvinyl polymer comprises between about 95 and about 99 weight percent of one or more carboxylic acid monomeric units, about 5 to about 1 weight percent of one or more acrylic esters monomeric units, and a small amount of crosslinked monomeric units, and a small amount of crosslinked monomeric units derived from polyalkenyl polyethers having more than one alkenyl ether group per molecule, the weight percentages of the monomeric units being based upon the total weight of the carboxy polymer, the carboxylic acid monomeric unit being derived from carboxylic acids selected from olefinically unsaturated acids defined as follows:

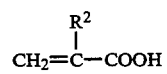

where $R_2$ is selected from hydrogen, halogens, cyanogen group—$C=N$, alkyl radicals of 1 to 4 carbon atoms, aryl radicals of 6 to 14 carbon atoms, aralkyl radicals of 7 to 14 carbon atoms, alkaryl radicals 7 to 12, and cycloaliphatic radicals of 4 to 8 carbon atoms; the acrylic ester monomeric units being derived from acrylic esters defined as follows:

$$\overset{R^2}{\underset{|}{CH_2=C}}-COOR^3$$

where $R_2$ is defined above in connection with said carboxylic acid and wherein $R^3$ is selected from alkyl groups of 10 to 30 carbon atoms.

Further according to the present invention, there is a method of shampooing and conditioning hair comprising applying the composition described above to wet hair and then rinsing the composition out of the hair.

Further according to the present invention, there is a process for making a shampoo-conditioning composition comprising in-line mixing an aqueous dispersion of the carboxyvinyl polymer described above with an aqueous shampooing agent surfactant solution.

Further according to the present invention, there is a shampoo-conditioning composition as described above wherein the shampooing agent is selected from the group consisting essentially of an anionic surfactant, a nonionic surfactant, and an amphoteric surfactant.

DETAILED DESCRIPTION OF THE INVENTION

Carboxyvinyl polymers useful in the present invention have carboxylic acid monomer units derived from olefinically unsaturated carboxylic acid monomers containing at least one activated carbon-to-carbon olefinic double bond, and at least one carboxyl group. The olefinic double bond readily functions in polymerization because of its presence in the monomer molecule either in the alpha-beta position with respect to a carboxyl group or as a part of a terminal methylene grouping, i.e., $CH_2<$. Olefinically unsaturated acids in this group include acrylic acids typified by the acrylic acid itself, methacrylic acid, ethacrylic acid, alpha-chloroacrylic acid, alpha-acrylic acid, beta methylacrylic acid (crotonic acid), alpha-phenyl acrylic acid, beta-acryloxy propionic acid, sorbic acid, alphachloro sorbic acid, angelic acid, cinnamic acid, p-chloro cinnamic acid, beta-styryl acrylic acid, itaconic acid, citraconic acid, mesaconic acid, glutaconic acid, aconitic acid, maleic acid, fumaric acid, and tricarboxy ethylene. As used herein, the term carboxylic acid includes anhydrides, as well as the polycarboxylic acids and those acid anhydrides, such as maleic anhydride, wherein the anhydride group is formed by the elimination of one molecule of water from two carboxyl groups located on the same polycarboxylic acid molecule.

Preferred carboxylic acid monomeric units are derived from acrylic acid monomers having the general structure $$\overset{R^1}{\underset{|}{CH_2=C}}-COOH$$

wherein $R^1$ is a substituent selected from the class consisting of hydrogen, halogen, and the cyanogen (C=N) groups, monovalent alkyl radicals of 1 to 4 carbons, monovalent aryl radicals of 6 to 14 carbons, monovalent alkaryl radicals of 7 to 12 carbons, and monovalent cycloaliphatic radicals of 4 to 8 carbons atoms. Of this class, acrylic, methacrylic, and ethacrylic acids are more preferred with acrylic acid being the most preferred. Another useful carboxylic monomer is maleic anhydride or the acid.

Suitable acrylic ester monomeric units are derived from acrylic ester monomers having the formula $$\overset{R^2}{\underset{|}{CH_2=C}}-\overset{O}{\underset{||}{C}}-O-R^3$$

where R is hydrogen, methyl or ethyl group and where $R^3$ is an alkyl group having 10 to 30 carbon atoms, preferably 12 to 22 carbon atoms. Representative acrylic esters include decyl acrylate, isodecyl acrylate, lauryl acrylate, dodecyl acrylate, stearyl acrylate, and the corresponding methacrylates. Mixtures of two or more of the long chain acrylic esters can be successfully polymerized with one or more of the carboxylic acids.

The carboxyvinyl polymers have crosslinking monomeric units derived from polyfunctional vinylidene monomers containing at least two terminal $CH_2-C<$ groups. Particularly useful crosslinking monomers are those polyalkenyl polyethers having more than one alkenyl ether group per molecule, and the most useful monomers have alkenyl groups in which an olefinic double bond is attached to a terminal methylene $CH_2-C<$. Such monomers can be prepared by the etherification of a polyhydric alcohol containing at least four carbon atoms and at least two hydroxyl groups. Products of such reactions are complex mixtures of polyethers with varying number of ether groups. It is preferred to use polyethers containing an average of two or more alkenyl ether groups per molecule. Other crosslinking monomers can also be used. Allyl pentaerythritol, trimethyolpropane diallylether, and allyl sucrose are exceptional crosslinking monomers for purposes herein.

The carboxyvinyl polymer preferably comprises from about 95 to about 99, and more preferably about 96 to about 98 weight percent of one or more of the carboxylic acid monomeric units and preferably about 5 to about 1, and more preferably about 4 to about 2 weight percent of one or more of the acrylic ester monomeric units. the carboxyvinyl polymer further preferably comprises a small proportion of the polyethylenically unsaturated crosslinking monomeric unit. The crosslinking monomeric unit is preferably from about 0.1 to about 1 and more preferably from about 0.1 to about 0.6 weight percent of the carboxyvinyl polymer. Preferred carboxyvinyl polymers useful to the present composition are Carbopol® 1342 and 1352; Pemulen® TR1 and TR2 (all of B. F. Goodrich & Co.). Carbopol® 1342 is most preferred.

Other vinylidene monomers can be used in place of the carboxylic acid in small amounts so 3long as the basic properties of the carboxyvinyl polymer such as thickening or a suspending are not adversely affected. examples include acrylonitrile, methacrylonitrile, acrylamide, methacrylamide, styrene, vinyl toluene, vinyl methyl ether, vinyl ethyl ketone, butadiene, vinyl acetate, methyl acrylate, butyl acrylate, cyanopropyl acrylate, methoxyethyl acrylate, chloroethyl acrylate, chloroethyl acrylate, vinyl chloride, vinylidene chloride, esters of maleic and fumaric acids bis (B-chloroethyl) vinyl phosphonates, and the like monomers that are known to those skilled in the art.

The carboxyvinyl polymers described herein have weight average molecular weights greater than about 500 to as high as several million. Molecular weight of such polymers is preferably in the range of about 100,000 to about 5 million.

Polymerization of the monomers may be carried out in the presence of a free radical catalyst in an inert atmosphere under pressure with proper agitation. Polymerization temperature may be varied from about 0° to about 125° C. with polymerization between about 25° to about 90° C. in presence of a free radical catalyst generally resulting in polymer yields of about 75 to about 100 percent. The monomers can be charged continuously or in batch during the course of polymerization or in any other conventional manner.

Useful free radical forming catalysts include peroxygen compounds such as sodium, potassium and ammonium persulfates, caprylyl peroxide, benzoyl peroxide, hydrogen peroxide, pelargonyl peroxide, cumene hydroperoxides, tertiary butyl diperphthalate, tertiary butyl perbenzoate, sodium peracetate, di(2-ethylhexyl)-peroxydicarbonate, and the like as well as azo catalysts such as axodiisobutyryl nitrile. Other useful catalysts include the so-called "redox" type of catalyst and the heavy-metal activated catalyst systems. Ultra-violet light may also be utilized as a source of free radicals. Although some systems polymerize solely by heat, catalysts generally provide better control.

Polymerization of the monomers is conducted a solvent or an inert organic liquid in which the monomers are soluble but the resulting polymer is insoluble. The polymerization medium can be a mixture of suitable organic liquids or solvents. The product is preferably obtained as a very fine friable or fluffy precipitate. Typical solvents include hydrocarbons containing 6 to 8 carbon atoms such as benzene, tetraline hexane, heptane, and cyclohexane; chlorinated solvents such as carbon tetrachloride, chloroform, trichloroethylene, methyl chloride ethyl chloride, and methylene chloride; chlorofluoroalkanes such as chlorofluoromethane and chlorofluoroethane containing at least 4 halogen atoms; esters such as methyl acetate and ethyl acetate; and alcohols including methanol, ethanol, butanol, and the like. Amount of organic medium used, normally will be in excess of the monomers to be polymerized and the proportion may vary from at least weight percent of monomers and 99 weight percent organic medium up to about 50 weight percent monomers and 50 weight percent medium.

The carboxyvinyl polymer preferably comprises between about 0.1 to about 1.5. more preferably between about 0.8 and about 1.0. and most preferably about 0.9 weight percent of the composition.

Excellent teachings directed to carboxyvinyl polymers useful in the present composition as well as methods of making are seen in U.S. Pat. No. 4,686,254, which is incorporated herein by reference.

The carboxyvinyl polymer may function as both a thickener for the composition and as a suspending agent for the oily conditioning agent. The carboxyvinyl polymer is present in an amount sufficient to suspend and stabilize the oily conditioning agent. The carboxyvinyl polymer is further preferably present in an amount and the carboxyl groups thereof are partially or substantially neutralized or esterified sufficient to thicken the composition to the desired level of thickening. The carboxyvinyl polymer is preferably about 30 to about 100 and more preferably about 70 to about 80 percent neutralized.

Suitable neutralizing agents for the carboxyvinyl polymer include those known in art as well as alkali anionic surfactants which provide the additional desired neutralizing effect. The neutralizing agent may be an organic or inorganic substance having a basic moiety capable of partially or substantially neutralizing the carboxyvinyl polymer. Useful neutralizing agents are seen in U.S. Pat. Nos. 3,330,731 and 3,590,005, which are incorporated herein by reference. Useful neutralizing agents include alkali and alkaline earth metal hydroxides; mono-, di-, and tri-aliphatic amines containing from 1 to about 20 carbon atoms in the aliphatic carbon chain with the same or different substituent groups in the di- and tri-compounds; and alkanolamines containing from 1 to about 12 carbon atoms in the alkyl group. Suitable alkali metal hydroxides include those of sodium, potassium, and lithium. Suitable alkanolamines include mono-, di-, and tri-ethanolamines, ethanolamines, propanolamines, isopropanolamines, and the like. A most preferred neutralizing agent is triethanolamine. Also useful as neutralizing agents are the anionic acyl sarcosine surfactants described below, which neutralize the carboxyvinyl polymer in addition to providing surface activity.

The present composition contains a cationic resin or surfactant as a cationic conditioning agent to enhance its conditioning performance. Preferably, the conditioning agent is a cationic resin or a ctionic surfactant having a weight average molecular weight of about 400 or greater and more preferably about 1000 to about 3 million. Suitable cationic resins and surfactants include the following: cationic or quaternized polysaccharides or polysaccharide derivatives, cationic or quaternized polyamides; cationic or quaternized polymeric derivatives of acrylates, methacrylates, acrylamides, methacrylamides, or copolymers thereof; and tetraalkylammonium salts and BO/PO/EO (butylene oxide/propylene oxide/ethylene oxide) derivatives thereof.

Suitable cationic or quaternized polysaccharides or polysaccharide derivatives include those of cellulosic polymers, guar gums, xanthan gums, locust bean gums, gum arabic starches, starch amyloses, alginates, and the like. Excellent teachings directed to useful polysaccharides and polysaccharide derivatives are seen in The Encyclopedia of Polymer Science and Engineering, 2 ed., vol. 7, pp. 589 to 613, which is incorporated herein by reference.

Particularly useful cationic or quaternized polysaccharides or polysaccharide derivatives are those of the guar gums and guar gum derivatives. Guar gums include those of high molecular weight carbohydrates or polysaccharides made up of linked mannose and galactose units. The molecule may be a straight chain of mannose units linked to each other by means of beta (1–4) glycosidic linkages. Galactose units may branch from alternate mannose units through alpha (1–6) linkages with the mannose units. Useful guar gums include cationic or quaternized derivatives of hydroxypropyl, hydroxyethyl, sodium carboxymethyl, and carboxymethylhydroxypropyl guar gums. A most preferred cationic guar gum resin is 2-hydroxypropyltrimonium chloride. Teachings directed to guar gums are seen in U.S. Pat. Nos. 4.678,606 and 4,491,539, both of which are incorporated herein by reference.

Other useful cationic or quaternized polysaccharides or polysaccharide derivatives include those of the cellulosic polymers such as methyl, ethyl, hydroxypropyl, hydroxyethyl, carboxymethyl, and carboxymethylhydroxypropyl cellulose. A representative quaternized cellulosic polymer is trimethylammonium hydroxyethylcellulose such as Polymer JR (Union Carbide Corp.).

Other cationic resins useful as conditioning agents include cationic or quaternized polyamides. Examples of such resins include cocodimonium hydrolyzed animal keratins such as Croquat WKP and steartrimonium hydrolyzed animal keratins such as Croquat Q (Croda Inc.).

Other cationic resins useful as conditioning agents include cationic or quaternized polymeric derivatives of acrylates, methacrylates, acrylamides, methacrylamides or copolymers, thereof as described by the following:

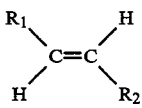

$R_1 = H, CH_3$
$R_2 = H$, Alkyl Radical, $-COOR_3$, $-COR_4$
$R_3 = C_1-C_{20}$ Saturated, unsaturated, branched or cycled alkyl radical

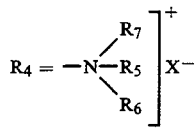

Examples of the above resins include dimethylaminoethylmethacrylate/vinyl pyrrolidone copolymers such as Gafquat 755 (GAF Corp.) and acrylamide/dimethyldiallylammonium chlorides such as Merquat 550 such as (Merck & Co.).

Other cationic resins useful as conditioning agents include cationic or quaternized polymeric derivatives of substituted allyl or vinyl compounds. Such compounds are of the general formula:

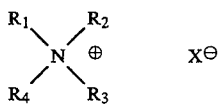

in which $R_1$ and $R_2$ are both vinyl radicals or both allyl radicals and $R_3$ and $R_4$ are the same or different and can be a lower alkyl or a fatty radical or represent a doubly bonded carbon of a cyclic residue containing $R_1$ or $R_2$ which may contain an additional heterocarbon, e.g. N, O or S. X is the counter ion, usually a halide such as bromide, chloride or iodide, and its identity is determined by the precursor raw materials known in the art. Said monomers can be copolymerized with either a monoethylenic compound such as ethylene, vinylbenzene, vinyl or allyl ester of acrylic or methacrylic acid more preferably vinyl pyrrolidone such as Luviquat FC-370 (BASF). Representative resins copolymerized with cellolosic derivatives include the Celquat polymers (National Starch and Chemical).

Other cationic resins and surfactants useful as conditioning agents include tetraalkylammonium salts and BO/PO/EO (butylene oxide/propylene oxide/ethylene oxide) derivatives thereof.

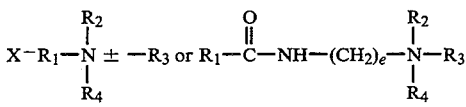

Where $X^- = Cl^-$, $CH_2CH_2OSO_2^-$, or other suitable anion $R_1 = C_{12}-C_{24}$ $R_2, R_3, R_4 =$

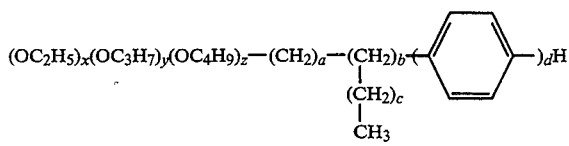

Where:
a=0-24  e=2-3
b=0-10  x=0-50
c=0-5   y=0-25
d=0-1   z=0-15

Suitable oily conditioning agents are oily, substantially water-insoluble substances which provide conditioning effects to the hair. These agents include, but are not limited to the following: mineral oils and saturated or unsaturated vegetable oils such as soybean oil, babassu oil, castor oil, cottonseed oil, Chinese tallow oil, crambe oil, perilla oil, Danish rapeseed, rice bran oil, palm oil, palm kernel oil, olive oil, linseed oil, coconut oil, sunflower oil, safflower oil, peanut oil, and corn oil. Preferred saturated and unsaturated vegetable oils are those having fatty acid components with 6 to 24 carbon atoms. More preferred saturated and unsaturated oils are those having 10 to 20 carbon atoms, with a most preferred composition containing 16 to 18 carbons. An example of the most preferred conditioning agent is soybean oil. The oily conditioning agent preferably comprises between about 0.1 to about 10, more preferably between about 0.5 to about 4 and most preferably about 0.5 to about 2.0 weight percent of the composition.

Additional oily conditioning agents include esters of the type

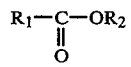

wherein $R_1$ and $R_2$ are saturated or unsaturated alkyl radicals of 3 to 24 carbon atoms. Suitable esters include isopropyl palmitate and butyl stearate.

The unexpected discovery that cationic conditioning agents could be made compatible with the anionic carboxyvinyl polymers described above has allowed a shampoo-conditioning composition to be formulated wherein both an oily and a cationic conditioning agent are present. The presence of both oily and cationic conditioning agents in the same composition results in a composition providing conditioning effects better than could expected from the additive conditioning effects of each agent individually.

One of the important aspects of this invention is the stability of oily and cationic conditioning agents with anionic carboxyvinyl polymers and the surfactant, particularly preferred anionic surfactants, of the present composition. The term "stability" in the present composition means that the oily and cationic conditioning agent remain substantially homogeneously suspended and dispersed in the composition.

The present composition may also be comprised of a silicone material to deliver some measure of softness and wet-combing and to aid in processing of the composition. The silicone materials may comprise preferably from about 0.1 to about 10 and more preferably from about 1 to about 4 weight percent of the composition.

The silicone material may be soluble or insoluble in water. Suitable water-insoluble silicone materials include polyalkylsiloxanes, polyarylsiloxanes, polyalkylarylsiloxanes, polysiloxane gums, and polyethersiloxane copolymers. Water-insoluble silicone materials may be considered oily conditioning agents as described previously. Teachings directed to suitable water-soluble and insoluble silicone materials are found in U.S. Pat. No. 4,788,006; U.S. Pat. Nos. 4,341,799; 4,152,416; 3,964,500; 3,208,911; 4,364,837 and U.S. Pat. No. 4,465,619, all of which are incorporated herein by reference. Suitable watersoluble silicones include polyether/polysiloxane block copolymers as represented by the formula.

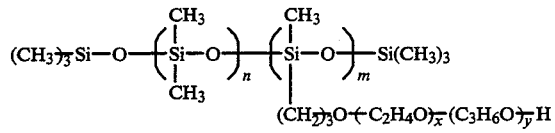

wherein n is from 10 to 80, m is From 0 to 50, x is From 20 to 100, y is from 0 to 80. In a most preferred silicone material, m=20, n=50, and x/y=77/23, as in Abil ® B88183 (trademark of Th. Goldschmidt AG). Examples of additional silicone materials includes Dow Corning 200, 345, and 3225C and General Electric SF-1202, SF18 (350) and others.

The present composition contains a shampooing agent comprising one or more surfactants, and functions to shampoo or clean the hair. The surfactants comprising the shampooing agent preferably comprise From about 5 to about 70, more preferably about 5 to about 20, and most preferably about 5 to about 12 active weight percent of the composition. Active weight percent refers to actual weight percent of the surfactant or surfactants in the composition, and not to the entire aqueous form in which the surfactant may be supplied for purposes of ease of formulation. The surfactant or surfactants may be anionic, nonionic, cationic, or amphoteric. Preferably, the surfactant or surfactants are anionic since they usually provide better cleaning and foaming than do the other types. For purposes of this specification, the anionic carboxyvinyl polymers described above are not considered shampooing agent surfactants. Cationic conditioning agents, whether cationic resins and cationic surfactants, are not considered shampooing agent surfactants in addition to being conditioning agents for purposes of this specification unless they have sufficient shampooing or cleaning efficacy to function as a shampooing agent standing alone in a typical commercial shampoo composition. Thus, a composition having a cationic resin or cationic surfactant functioning primarily as a conditioning agent rather than a shampooing agent may also have other lighter cationic surfactants, preferably those with a weight average molecular weight of less than about 400, which function primarily as shampooing agents.

Suitable anionic surfactants include alkyl and alkyl ether sulfates, or combinations thereof. These surfactants have the respective formula $ROSO_3M$ and $RO-(C_2H_4O)_xSO_3M$ wherein R is an alkyl or alkenyl radical of preferably about 8 to about 22 and, more preferably about 10 to about 18 carbon atoms, x is 0 to 10 and M a water-soluble cation such as ammonium, sodium, potassium, and triethanolamine. A most preferred alkyl sulfate is R=12-14, and M=$NH_4$ cation (ammonium lauryl sulfate).

Other suitable anionic surfactants include acyl sarcosines derived from natural fatty acids and amino acid sarcosine (N-methyl glycine) of the following formula

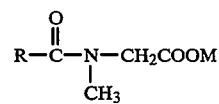

where R is a Fatty acid hydrocarbon chain from 10 to 20 carbon atoms, and M is a water-soluble cation such as ammonium, sodium, potassium, triethanolamine, etc. Common derivatives include lauroyl, myristoyl, oleoyl, and stearoyl sarcosinates. Fatty acid sarconsine surfactants, particularly sodium lauroyl sarcosinate, are preferred because they neutralize the carboxyvinyl polymer in addition to functioning as an anionic surfactant and a pH adjuster.

Other suitable anionic surfactants include alkyl and alkylbenzene sulfonates and succinates and sulfosuccinates having from about 8 to about 24 carbon atoms. Suitable derivatives include the ammonium, sodium, potassium, and triethanolamine salts thereof.

Many varieties of suitable anionic surfactants as well as other types of surfactants are disclosed in U.S. Pat. Nos. 3,723,357; 4,788,006; 4,364,837 and 4,491,539, all of which are incorporated herein by reference.

The present composition preferably has a pH from about 4 to about 10 and more preferably from about 4 to about 6.

Water is an essential component of the present composition, and comprises preferably from about 30 to about 90 and more preferably from about 60 to about 80 weight percent of the composition.

The present composition may further include optional ingredients such as preservatives, pearlescing agents, antidandruff agents, pH adjusting agents, perfumes, colorants, opacifiers and the like.

There is also a method according to the present invention for applying the present composition to the hair comprising applying about 0.1 to about 10 grams of the present composition to wettened hair and then rinsing it out of the hair.

There is also a process according to the present invention for making the present composition comprising in-line mixing of an aqueous dispersion of the carboxyvinyl polymer and a solution of the shampooing agent, which is preferably one or more surfactants and more preferably one or more anionic surfactants. An important aspect of the present invention is how the carboxyvinyl polymer dispersion and the shampooing agent solution, are admixed. In-line mixing of the copolymer dispersion and the shampooing agent solution minimizes formation of insoluble gel particles of the carboxyvinyl polymer possibly resulting from its incompatibility with the shampooing agent. In-line mixing is a process for mixing or blending wherein two fluids are simultaneously pumped in certain mass ratios through an in-line mixer as opposed to batch mixing, wherein batch quantities of two fluids are combined at substantially the same time and subsequently mixed or blended. The in-line method of mixing is particularly advantageous for production of commercial quantities of the present composition. The preferred temperature range for simultaneous mixing is about 65° to about 75° F.

Another important aspect of the present process is the incorporation of the cationic conditioning agent into the present composition. A suspension of the cationic conditioning agent is mixed or blended with the shampooing agent solution prior to the in-line blending of the shampooing agent solution and the carboxyvinyl polymer dispersion. The cationic suspension and the shampooing agent solution may be blended by any conventional means, including batch mixing or in-line mixing. The presence of the shampooing agent allows the cationic conditioning agent to be dispersed within the carboxyvinyl polymer dispersion, which is substantially anionic, without the compatibility problems typically encountered with blending of cationic and anionic materials.

The oily conditioning agent may be admixed with either of the carboxyvinyl copolymer dispersion or the cationic conditioning agent suspension. How the oily conditioning agent is mixed into the present composition is not critical, and may be effected by either simultaneous mixing or by conventional batch mixing.

Water-soluble silicone materials are preferably incorporated into the present composition by admixing into the cationic conditioning agent suspension.

The various suspensions and dispersions described above may be formed by any means known in the art such as mixers, agitators, and blenders. The blending may be accomplished by a combination of agitation and heating or by agitation alone. The present composition may be formed on either a bench scale or a commercial manufacturing scale.

The invention may be more fully understood by reference to the following examples which illustrate, but by no means, limit the scope of the invention.

EXAMPLES

Example 1

Shampoo-conditioning compositions of the present invention indicated as samples in Table 1 were prepared and subjected to accelerated stability testing known in the art to assess stability. All 15 samples represented in Table 1 were found to be stable after four weeks at 45° C.

TABLE 1

| COMPONENT | I | II | III | IV | V | VI | VII | VIII | IX | X | XI | XII | XIII | XIV | XV |
|---|---|---|---|---|---|---|---|---|---|---|---|---|---|---|---|
| NH4C12-18 Alkyl Sulfate (28% active by weight) | 40 | 40 | 40 | 40 | 40 | 40 | 40 | 50 | 40 | 40 | 40 | 40 | 40 | 40 | 40 |
| Carbopol ® 1342 | 1.0 | 1.0 | 1.0 | 1.0 | 0.9 | 0.9 | 0.9 | 1.0 | 0.9 | 0.9 | 0.9 | .10 | 1.0 | 1.0 | 1.0 |
| Soybean Oil | 2.0 | 2.0 | — | 2.0 | 2.0 | 1.0 | 0.5 | — | 2.0 | 2.0 | 2.0 | 2.0 | 2.0 | 2.0 | 2.0 |
| Coconut Oil | — | — | 2.0 | — | — | — | — | 2.0 | — | — | — | — | — | — | — |
| Guar Hydroxy Propyl Trimonium Chloride | 0.3 | 0.3 | 0.2 | 0.1 | 0.1 | 0.1 | 0.1 | 0.1 | 0.1 | — | — | 0.1 | 0.1 | 0.1 | 0.1 |
| Linoleamide DEA | 2.0 | — | — | — | — | — | — | — | — | — | — | — | — | — | — |
| Polyquaternium-7 (Merquat 550) | — | — | — | — | — | — | — | — | — | 5.0 | — | — | — | — | — |
| Polyvinylpyrolidone | — | — | — | — | — | — | — | — | — | — | 0.5 | — | — | — | — |
| Dimethicone Copolyol | 2.0 | 2.0 | 2.0 | 2.0 | 2.0 | 2.0 | 2.0 | 2.0 | 2.0 | 2.0 | 2.0 | — | 2.0 | 2.0 | 2.0 |
| Dimethicone | — | — | — | — | — | — | — | — | — | — | — | 2.0 | — | — | — |
| Sodium Lauroyl Sarcosinate | 8.0 | 8.0 | 8.0 | 5.0 | 2.0 | 2.0 | 2.0 | 5.0 | 5.0 | 5.0 | 5.0 | 5.0 | — | 8.0 | 8.0 |
| Triethanolamine | — | — | — | 0.9 | 0.9 | 0.9 | 0.9 | — | 0.9 | 0.9 | 0.9 | 0.9 | 1.5 | — | — |
| Phosphoric Acid | — | — | — | — | — | — | — | — | — | — | — | — | 0.1 | — | — |
| Citric Acid | — | 0.08 | 0.08 | 0.08 | 0.08 | 0.08 | 0.08 | 0.08 | 0.08 | 0.08 | 0.08 | 0.08 | — | — | — |
| Ethylene glycol distearate (EGDS) | — | — | — | 1.0 | 1.0 | 1.0 | 1.0 | — | 1.0 | 1.0 | 1.0 | — | 1.0 | — | — |
| Fragrance | — | — | — | — | 0.7 | 0.7 | 0.7 | — | — | — | — | — | 0.8 | — | — |
| Water | * | * | * | * | * | * | * | * | * | * | * | * | * | * | * |
| Isopropyl Palmitate (Wickenol III) | — | — | — | — | — | — | — | — | — | — | — | — | — | 2.0 | — |
| Butyl Stearate (Emerest 2325) | — | — | — | — | — | — | — | — | — | — | — | — | — | — | 2.0 |

*qs 100 (remainder water)

Example 2

Ease of combing of formula Samples I, II and IX from Example 1 was evaluated on virgin, brown hair tresses (DeMeo Brothers) vs. a control composition described below.

Approximately 1.25 grams of each formula sample were applied to 2 grams of hair previously treated with a TEA lauryl sulfate/sodium laural sulfate solution to remove any residual oils. The formulas were massaged into the hair for one minute and rinsed from the hair for two minutes using 45° C. water.

The hair tresses were evaluated for ease of wet and dry combing (resistance to downward force of comb) by combing through the tresses with a rubber comb. Ease of wet combing was determined after the rinse step described above. After tangles were removed, the hair was dried for at least 2 hours to ensure substantially complete water removal and then tested for dry combing. A relative rating system for both of the tests on a scale of 1 to 5 is shown below 5 =Extreme ease of combing through hair; very slight force required.

1=Extreme difficulty of combing through hair; extreme force required.

The enhancement in both wet and dry combing in the test compositions versus that of the control composition is manifest in the test results indicated in Table 2.

TABLE 2

EASE OF WET AND DRY COMBING

| FORMULA | EASE OF WET COMB | EASE OF DRY COMB |
|---|---|---|
| I | 4.75 | 4.5 |
| II | 4.75 | 4.5 |
| IX | 4.2 | 4.4 |
| CONTROL I | 2.2 | 3.6 |

COMPOSITION = AMMONIUM LAURYL
SULFATE - 28.0%
COCAMIDOPROPYL BETAINE - 2.5%
LAURAMIDE DEA - 1.5%
HYDROXYPROPYL METHYL-
CELLULOSE - 0.2%
QS 100% WATER

Example 3

Formula compositions II, V, VI and VII of Example 1 were tested for wet and dry combing and static charge generation versus the control composition seen in Table 2 using the in vivo method described herein.

Half-head evaluations comparing the test and the control compositions were conducted by salon operators on 20 people. The test and control compositions were randomly assigned to right and left sides of the heads. Evaluators measured the difference in above-described properties between the two sides of the head. A numerical rating of from 0–4 was assigned to that difference.

The enhancement in both wet and dry combing in the test compositions versus that of the control composition is manifest in the test results indicated in Table 3.

1. Powder Dispersion—Disperse Carbopol® 1342 into Tank 2 into 50.5 weight percent water using a Zyclon Disperser with Quadro Vac attachment and a cold water supply operating at approximately 30±5 gal./min.
2. Batch Homogenization—Initiate mixing at approximately 25 RPM. Add a 3.5% phosphoric acid solution (1% water, 0.035% phosphoric acid) and mix for one hour minimum until completely homogeneous.

C) LINE BLENDING
  1. Simultaneously pump the SURFACTANT PHASE at 25.0±1.5 gal./min. and the CARBOPOL PHASE at 32.5±1.5 gal./min. through a Lightnin Line Blender and filter through a cartridge filter into Tank 3

D) FINAL BATCHING (Tank 3)
  1. Deaeration
     a. Initiate turbine mixing at 97 RPM and scraper mixing at 5 RPM in Tank 3. Heat to 68°–71° C.
     b. Shut off heating. Turn off scraper agitator and reduce turbine speed to 35 RPM to deaerate batch.
  2. Oil Addition
     a. Set mixer speeds at 97 RPM turbine, 5 RPM scraper.
     b. Add 2 weight percent soybean oil and 1 weight percent ethylene glycol distearate, mix until completely dispersed.
     c. Cool to 41°–43° C. add 0.8 weight percent fragrance and 1.5 weight percent triethanolamine.

What is claimed is:

TABLE 3

Ease of Wet and Dry Combing - Salon Evaluation

| SAMPLE A | AVG. DIFFERENCE IN WET COMB | STATISTICAL SIGNIFICANCE | AVG. DIFFERENCE IN DRY COMB | STATISTICAL SIGNIFICANCE | AVG. DIFFERENCE IN STATIC | STATISTICAL SIGNIFICANCE |
|---|---|---|---|---|---|---|
| II | 2.89 | >99.9 | 2.0 | >99.9 | 0.85 | 99.9 |
| V | 2.2 | >99.9 | 2.0 | >99.9 | 0.80 | 98.0 |
| VI | 2.1 | >99.9 | 1.5 | >99.7 | — | — |
| VII | 1.9 | >99.9 | 1.5 | >99.9 | — | — |

Example 4

A composition of the present invention can be prepared as outlined below. All weight percents are relative to the total weight of the composition as a finished product unless otherwise indicated.

A) SURFACTANT PHASE (Tank 1)
  1. Mix 2.0 weight percent of the Dimethicone Copolyol (ABIL®B88183) and 40 weight percent of ammonium lauryl sulfate (28 percent active in water) together in a tank using a pitched blade turbine operating at approximately 35 RPM.
  2. In a separate premix tank substantially disperse 0.1 weight percent the cationic resin (Cosmedia Guar C 261) into 1.0 weight percent of the water of the composition.
  3. With continued mixing, add the cationic resin premix to the surfactant phase.
  4. Increase mixing speed to approximately 45 RPM.
  5. Heat to 71°–74° C. (using hot water heat).
  6. Reduce speed to 10 RPM and continue to mix for 1 hour.
  7. Cool batch to 8°–21° C., still mixing at 10 RPM.
  8. At 18°–21° C., shut off cooling and mixing.

B) CARBOXYVINYL POLYMER PHASE (Tank 2)

1. A shampoo-conditioning composition, comprising:
   A) from about 0.1 to about 10 percent of the composition of an oily, water-insoluble conditioning agent selected from a group consisting of mineral oils; saturated or unsaturated vegetable oils selected from the group consisting of peanut oil, corn oil, coconut oil, and soybean oil; alkyl esters of fatty acids; and polyalkylsiloxanes, polyarylsiloxanes, polyalkylarylsiloxanes, polysiloxane gums, and polyethersiloxane copolymers;
   B) from about 5 to about 70 active weight percent of the composition of one or more anionic surfactants selected from the group consisting of alkyl sulfates, alkyl ether sulfates, alkaryl sulphonates, alkyl succinates, alkyl sulphosuccinates, N-alkoyl sarcosinate, alkyl phosphates, and alkyl ether phosphates, wherein the alkyl group contains from 8 to 22 carbons and may be unsaturated;
   C) from about 0.1 to about 1.5 weight percent of the composition of a carboxyvinyl polymer to suspend and stabilize the oily conditioning agent, the carboxyvinylpolymer comprising between about 95 and about 99 weight percent of one or more carboxylic acid monomeric units about 5 to about 1 weight percent of one or more acrylic esters monomeric units, and a small amount of crosslinked monomeric units derived from polyalkenyl polyethers having more than one alkenyl ether group per molecule, the weight percentages of the monomeric units being based upon the total weight of the carboxypolymer, the carboxylic acid monomeric unit being derived from carboxylic acids selected from olefinically unsaturated acids defined as follows:

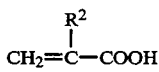

$$CH_2=\underset{\underset{R^2}{|}}{C}-COOH$$

where $R_2$ is selected from hydrogen, halogens, cyanogen group $-C\equiv N$, alkyl radicals of 1 to 4 carbon atoms, aryl radicals of 6 to 14 carbon atoms, aralkyl radicals of 7 to 14 carbon atoms, alkaryl radicals 7 to 12, and cycloaliphatic radicals of 4 to 8 carbon atoms; the acrylic ester monomeric units being derived from acrylic esters defined as follows:

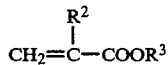

$$CH_2=\underset{\underset{R^2}{|}}{C}-COOR^3$$

where $R_2$ is defined above in connection with said carboxylic acid and wherein $R^3$ is selected from alkyl groups of 10 to 30 carbon atoms;

D) from about 0.1 to about 10 weight percent of the composition of a cationic conditioning agent selected from a group consisting of cationic or quaternized polysaccharides or polysaccharide derivates, cationic or quaternized polyamides, cationic or quaternized polymeric derivatives of acrylates, methacrylates, acrylamides, methacrylamides, or copolymers thereof, and tetraalkylammonium salts and butylene/propylene/ethylene oxide derivatives thereof; and E) from about 30 to about 90 weight percent of the composition of water.

2. The composition according to claim 1, wherein the cationic conditioning agent is a cationic resin of molecular weight from about 1,000 to about three million.

3. The composition according to claim 1, wherein the carboxyvinyl polymer is neutralized.

4. The composition of claim 1, wherein the anionic surfactant comprises from about 5 to about 20 active weight percent of the composition.

5. The composition of claim 1, wherein the anionic surfactant comprises from about 5 to about 12 active weight percent of the composition.

6. The composition of claim 1, wherein the vegetable oil is soybean oil.

7. The composition of claim 1, wherein the vegetable oil is between about 1.0 to about 4.0 weight percent of the composition.

8. The composition of claim 1, wherein the carboxyvinyl copolymer comprises from about 0.8 to 1.0 weight percent of composition.

9. The composition of claim 1, wherein the crosslinking monomeric unit comprises about 0.1 to about 0.6 weight percent of the carboxyvinyl copolymer.

10. The composition of claim 1 wherein the cationic resin is guar hydroxypropyltrimonium chloride.

11. The composition of claim 1, wherein the cationic conditioning agent comprises from about 0.1 to about 2.5 weight percent of the composition.

12. The composition of claim 1, wherein the anionic surfactant is ammonium lauryl sulfate.

13. The composition of claim 1, wherein the composition further comprises a silicone.

14. A process for making a shampoo-conditioning composition, comprising; mixing an aqueous dispersion of the carboxyvinyl polymer described in claim 1 with an aqueous surfactant solution.

15. The process of claim 14, wherein a suspension of a cationic conditioning agent is mixed with the surfactant solution prior to the mixing of the carboxyvinyl polymer dispersion and the surfactant solution.

16. A method of shampooing and conditioning hairs comprising: applying the composition of claim 1 to wet hair and then rinsing the composition out of the hair.

17. The composition of claim 1 wherein Component A) includes a water-soluble polyether/polysiloxane block copolymer.

* * * * *